United States Patent [19]

McQueen et al.

[11] Patent Number: 5,026,391

[45] Date of Patent: Jun. 25, 1991

[54] CURVED BUTTERFLY BILEAFLET PROSTHETIC CARDIAC VALVE

[76] Inventors: David M. McQueen, 185 Hillside Ave., Chatham, N.J. 07928; Charles S. Peskin, 186 Harrard Dr., Hartsdale, N.Y. 10530

[21] Appl. No.: 434,621

[22] Filed: Nov. 14, 1989

Related U.S. Application Data

[63] Continuation of Ser. No. 758,611, Jul. 24, 1985, abandoned.

[51] Int. Cl.⁵ ................................. A61F 2/24
[52] U.S. Cl. ..................... 623/2; 137/512.1; 137/527
[58] Field of Search ............................................ 623/2

[56] References Cited

U.S. PATENT DOCUMENTS

| | | | |
|---|---|---|---|
| 4,263,680 | 4/1981 | Reul et al. | 623/2 |
| 4,689,046 | 8/1987 | Bokros | 623/2 |
| 4,822,353 | 4/1989 | Bokros | 623/2 |
| 4,846,307 | 7/1989 | Knoch et al. | 623/2 |
| 4,863,459 | 9/1989 | Olin | 623/2 |
| 4,872,875 | 10/1989 | Hwang | 623/2 |

FOREIGN PATENT DOCUMENTS 0843976 7/1981 U.S.S.R. ................................. 623/2

OTHER PUBLICATIONS

"Computer Design of Mitral Valve Prostheses," McQueen & Peskin, vol. 1 of the Proceedings of SECTAM XII, May 1984.
"Modeling Prosthetic Heart Valves for Numerical Analysis of Blood Flow in the Heart", by Peskin & McQueen, Journal of Computational Physics, vol. 37, #1, Aug. 1980.
"Fluid Dynamics of the Mitral Valve: Physiological Aspects of a Mathematical Model", McQueen, Peskin & Yellin, American Physiological Journal, 242, 1982.
"Design to Manufacture of the St. Jude Prosthetic Heart Valve", Hansen, U. of Texas, Colloquium, Sep. 1979.
"Computer-Assisted Design of Pivoting Disc Prosthetic Mitral Valves", McQueen & Peskin, Journal of Thoracic and Cardiovascular Surgery, vol. 86, #1, Jul. 1983.

Primary Examiner—David J. Isabella
Assistant Examiner—Stephanie L. Iantorno
Attorney, Agent, or Firm—Fulbright & Jaworski

[57] ABSTRACT

An annular valve body having a central passageway for the flow of blood therethrough with two curved leaflets each of which is pivotally supported on an accentric positioned axis in the central passageway for moving between a closed position and an open position. The leaflets are curved in a plane normal to the eccentric axis and positioned with the convex side of the leaflets facing each other when the leaflets are in the open position. Various parameters such as the curvature of the leaflets, the location of the eccentric axis, and the maximum opening angle of the leaflets are optimized according to the following performance criteria: maximize the minimum peak velocity through the valve, maximize the net stroke volume, and minimize the mean forward pressure difference, thereby reducing thrombosis and improving the hemodynamic performance.

5 Claims, 9 Drawing Sheets

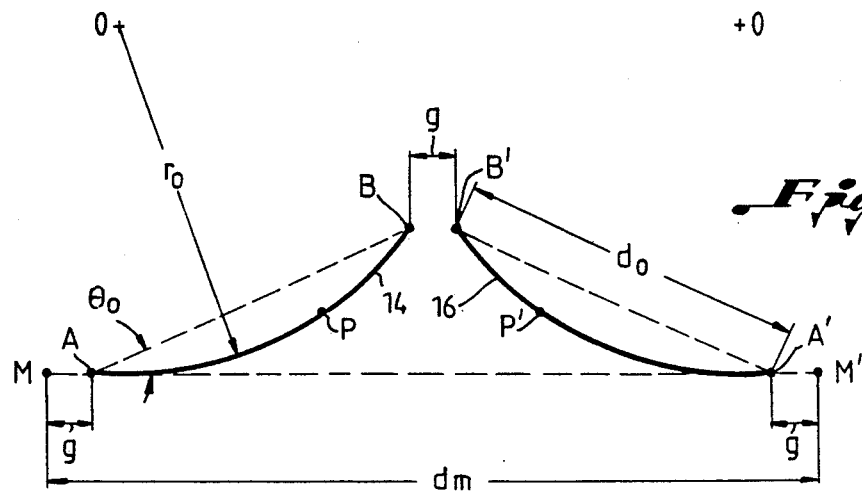
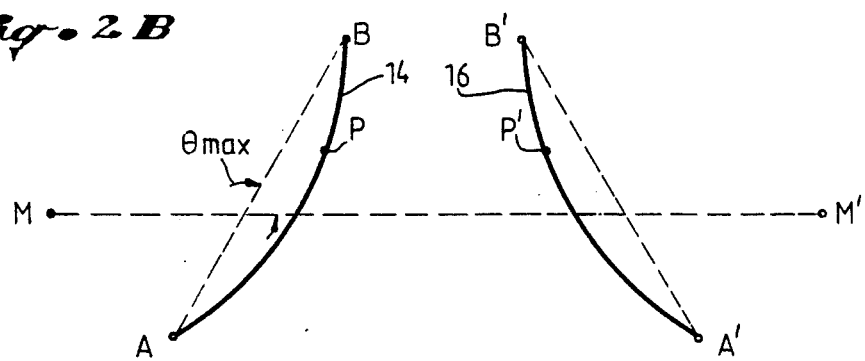
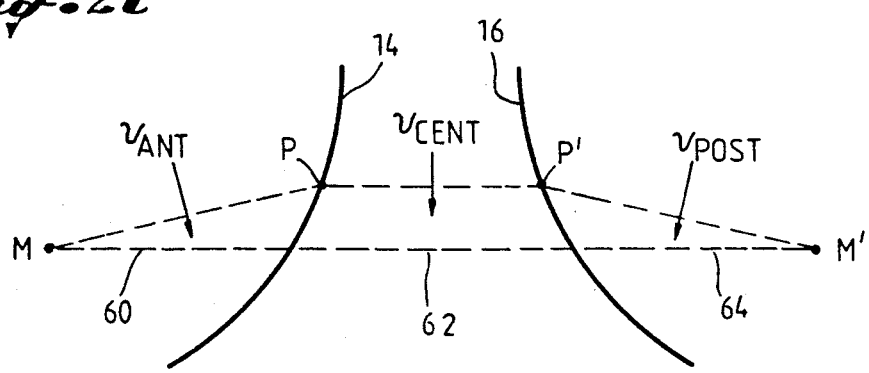

TABLE I
PIVOT POINT THAT MAXIMIZES $V^*_{MIN.}$ AT EACH CURVATURE

| MAX. OPENING ANGLE $\theta_{MAX.}$ | CURVATURE C | PIVOT POINT $S_P^{}(C)$ | MINIMUM PEAK VELOCITY $V^{}_{MIN.}(C)$ |
|---|---|---|---|
| 85° | 0. | 0.667 | 26.89 |
|  | 0.500 | 0.667 | 37.00 |
|  | 0.583 | 0.671 | 37.10 |
|  | 0.667 | 0.674 | 37.08 |
|  | 0.750 | 0.677 | 36.95 |
| 90° | 0. | 0.667 | 29.16 |
|  | 0.333 | 0.660 | 37.11 |
|  | 0.417 | 0.655 | 38.52 |
|  | 0.500 | 0.658 | 39.05 |
|  | 0.583 | 0.660 | 38.90 |
|  | 0.667 | 0.661 | 38.72 |
|  | 0.750 | 0.661 | 38.45 |

Fig.-12A

TABLE II
PARAMETERS THAT MAXIMIZE $V^*_{MIN}$

| MAX. OPENING ANGLE $\theta_{MAX.}$ | CURVATURE $C_{OPT.}$ | PIVOT POINT $S_P^{}(C_{OPT.})$ | MINIMUM PEAK VELOCITY $V^{}_{MIN.}(C_{OPT.})$ |
|---|---|---|---|
| 85° | 0.583 | 0.671 | 37.10 |
| 90° | 0.500 | 0.658 | 39.05 |

Fig.-12B

TABLE III
PARAMETERS THAT MAXIMIZE $SV/\overline{\Delta p}$

| MAX. OPENING ANGLE $\theta_{MAX.}$ | CURVATURE | PIVOT POINT | BENEFIT/COST $SV/\overline{\Delta p}$ |
|---|---|---|---|
| 85° | 0.750 | 0.667 | 7.73 |
| 90° | 0.583 | 0.667 | 7.97 |

Fig.-12C

CURVED BUTTERFLY BILEAFLET PROSTHETIC CARDIAC VALVE

BACKGROUND OF THE INVENTION

This invention was made under a research grant HL17859 of the National Institutes of Health and supported in part by the Department of Energy under Contract DE-AC02-76ER0377.

This application is a continuation of application Ser. No. 06/758,611, filed July 24, 1985, now abandoned.

Various types of heart valve prostheses have been developed which operate hemodynamically as a result of the pumping action of the heart in which they generally function as check valves. Such valves have taken the form of a ball and cage arrangement, or use one or more plates or discs. One type of valve commercially available is the St. Jude valve using two flat leaflets, and another type is the Hemex valve which is a bileaflet valve in which the leaflets are curved in a plane parallel to the pivot axis of the leaflets.

The number of heart valves being used is increasing and as human life depends upon the functioning of these valves, it is important that these prosthetic cardiac valves be improved and optimized as much as possible.

The present invention is directed to a curved butterfly bileaflet valve in which the shape and design criteria are selected to maximize the minimum peak velocity through the various compartments of the valve for reducing stagnant blood flow which may lead to valve thrombosis, and to improve the hemodynamic performance by increasing the net stroke volume and decreasing the mean forward pressure difference.

SUMMARY OF THE INVENTION

The present invention is directed to a heart valve prosthesis having an annular valve body with a central passageway for the flow of blood therethrough from upstream to downstream. First and second curved leaflets are pivotally supported in the central passageway of the body for moving between a closed position blocking blood flow through the passageway and an open position allowing blood flow therethrough. Each curved leaflet has a concave and a convex side. Eccentric position axis means are provided for pivotally supporting each of the leaflets. The leaflets are curved in a plane normal to the eccentric axis and positioned with the convex sides of the leaflets facing each other when the leaflets are in the open position.

Another object of the present invention is wherein the concave sides of the leaflets face upstream when in the closed position.

Still a further object is wherein the leaflets are circularly curved.

A still further object of the present invention is the provision of means in the body for limiting the maximum angle of opening of the leaflets to no more than approximately 90 degrees from a transverse plane to the central passageway.

Yet a further object of the present invention is wherein the first and second leaflets are pivotally supported along an axis located approximately two-thirds of the greatest distance form an arcuate body-contacting edge to a leaflet-mating edge of each leaflet.

Yet a still further object of the present invention is wherein the curvature of the curved leaflets is circular and is of a value to maximize the minimum peak velocity flowing between the leaflets and on the outside of each leaflet.

Other and further objects, features and advantages will be apparent from the following description of a presently preferred embodiment of the invention, given for the purpose of disclosure and taken in conjunction with the accompanying drawings.

BRIEF DESCRIPTION OF THE DRAWINGS

FIGS. 2A, 2B and 2C are schematic views of the butterfly bileaflet valve of the present invention for illustrating the design of various parameters, FIG. 12A, 12B and 12C are respectively tables I, II and III of various data.

DESCRIPTION OF THE PREFERRED EMBODIMENT

Figure 13:
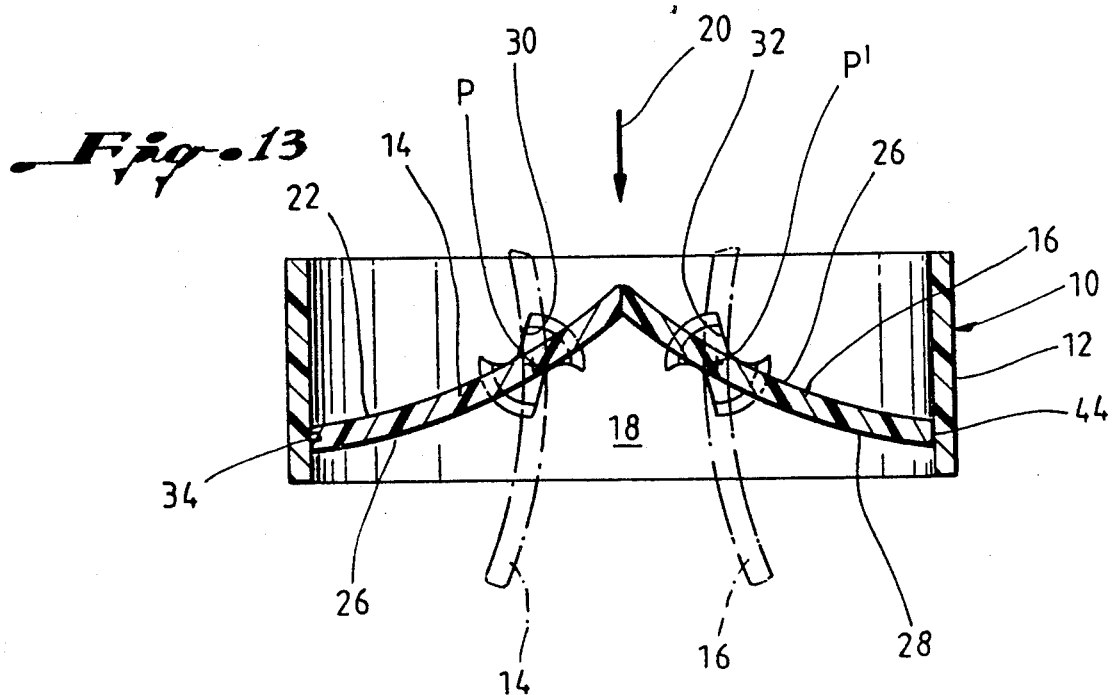
FIG. 13 is an elevational view, in cross section, of a preferred embodiment of the curved butterfly bileaflet valve of the present invention.
Figure 14:
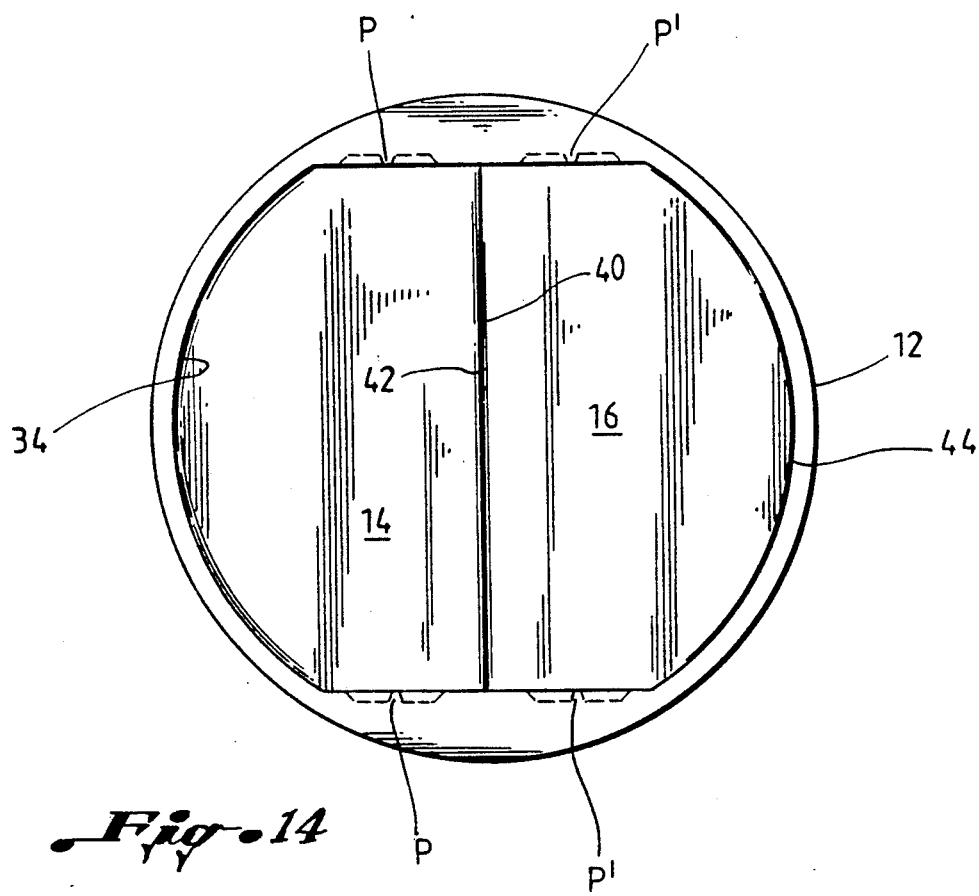
FIG. 14 is a cross-sectional view taken along the line 14—14 of FIG. 13.

Referring now to the drawings, and particularly to FIGS. 13 and 14, the curved butterfly bileaflet prosthetic cardiac valve of the present invention is generally indicated by the reference numeral 10 and includes an annular body or housing 12 which supports first and second pivoting leaflets or occluders 14 and 16 that open and close to control the flow of blood through a central passageway 18. The normal flow of blood through the valve 10 is in the direction of the arrow 20. Any suitable means may be connected to the body 12 for attaching a suturing ring to the annular body 12 to facilitate sewing the valve 10 to the heart tissue as is conventional.

The valve housing 12 and leaflets 14 and 16 may be made of any suitable material that is biocompatible and non-thrombogenic. For example, the body 12 and leaflets 14 and 16 may be made of isotropic graphite which is suitably coated with pryolitic carbon.

The leaflets 14 and 16 are each pivotally supported on an eccentric positioned axis at pivot points P and P', respectively. The leaflets 14 and 16 are curved in a plane normal to the eccentric axis. The leaflets 14 and 16 have a concave side 22 and 24, respectively, and a convex side 26 and 28, respectively. The convex sides 26 and 28 face each other when the leaflets 14 and 16 are in the open position and the concave sides 22 and 24 face upstream when the valve is in the closed position. Preferably, the curve of the leaflets 14 and 16 is circular and preferably the leaflets 14 and 16 are flat in a plane parallel to the eccentric axis although the leaflets 14 and 16 could also be curved in a plane parallel to the pivot axis.

The body 12 may include stop shoulders 30 and 32 positioned in the path of movement of the leaflets 14 and 16, respectively, for limiting the maximum opening angle of the leaflets 14 and 16 as will be more fully discussed hereinafter. The leaflets 14 and 16 are generally semi-circular in cross section and are adapted to engage and seat on a valve seat 34 in the body 12 when in the closed position by the outside edges 36 and 44 of the leaflets 14 and 16, respectively. The inside edges 40 and 42 are positioned to engage each other when the valve is in the closed position. Blood flowing in the direction of the arrow 20 from upstream to downstream will open the leaflets 14 and 16 until they reach their shoulder stops 30 and 32, respectively. When the downstream flow of blood is discontinued, the back pressure which is present will cause the leaflets 14 and 16 to swing or pivot around the pivot points P and P', respectively, towards the closed position.

As in the prior art valves using two flat leaflets, the present valve 10 when opened has three separate channels for forward blood flow, that is, two lateral channels and one central channel. However, both physical studies measurements and computer studies show that the blood flow in the central channel of the prior art flat leaflets tends to be stagnant relative to the flow in the lateral channels of the valve. Stagnant flow is dangerous because it may lead to valve thrombosis. One of the features of the present invention is the reduction of this problem by curving the valve leaflets 14 and 16 as described above to form a central venturi channel which helps open the leaflets 14 and 16 and also funnels flow into the previously stagnant central channel of the valve.

In addition, various parameters have been considered to improve the performance of the valve 10 to select an optimal valve that not only maximizes the minimum peak velocity in any of the flow channels, but also maximizes the net stroke volume of blood crossing the valve per heart beat and minimizes the mean pressure difference during forward flow, thereby improving the hemodynamic performance. In order to provide an optimal valve, the parameters considered are the position of the pivot points P and P', the radius of curvature of the leaflets 14 and 16, and the opening angle of the leaflets 14 and 16. A computer was used to define the parameters of a model valve and the performance criteria that are used to select an optimal valve.

Figure 1B:
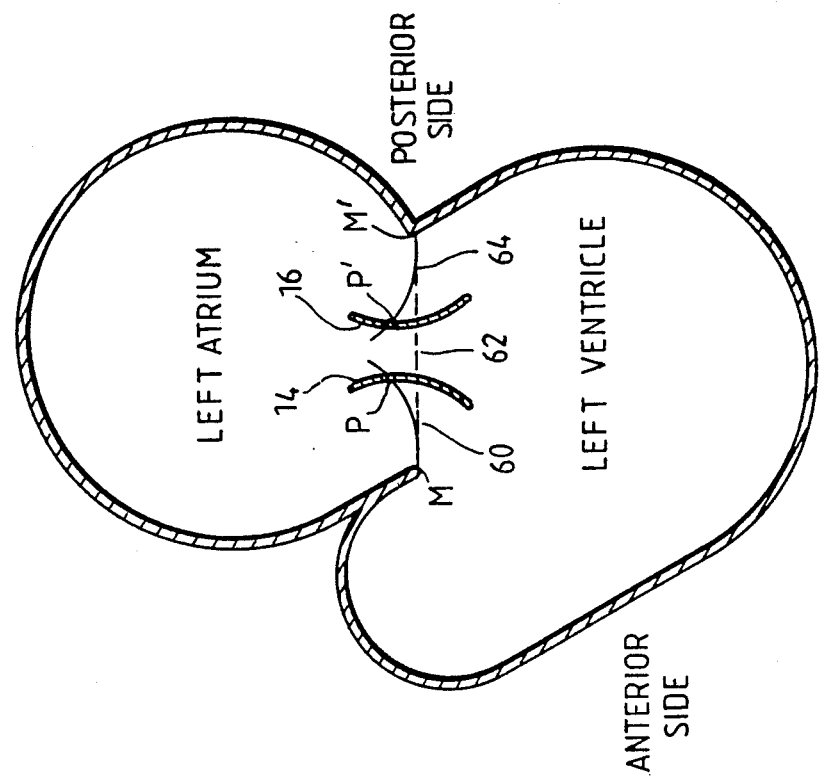
FIG. 1B is a view similar to FIG. 1A but showing the curved leaflets of the present invention.
Figure 1A:
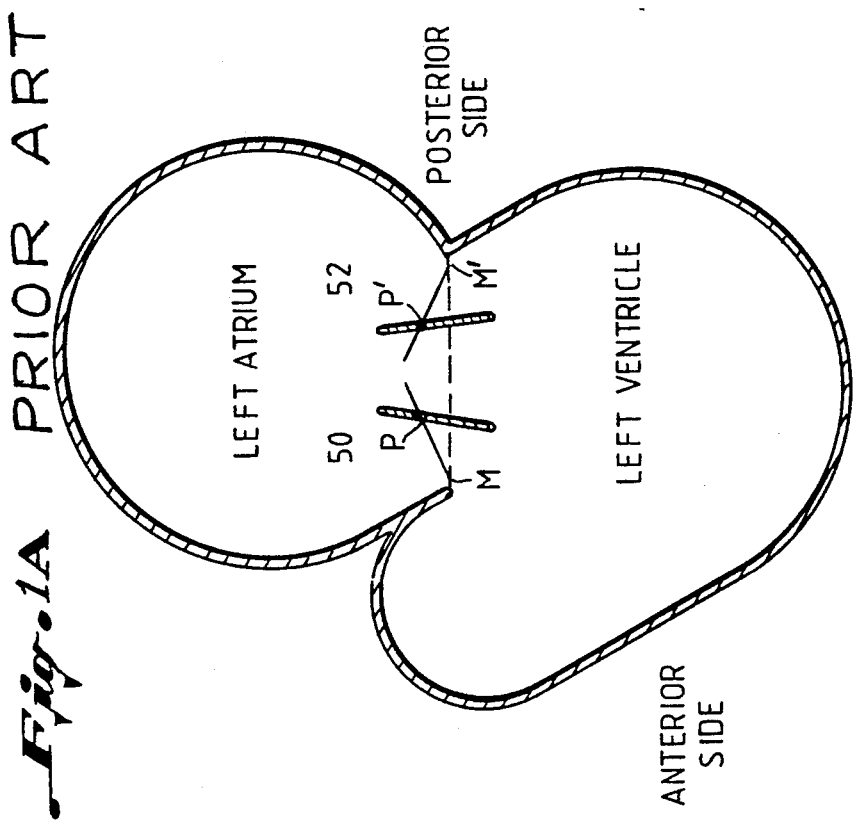
FIG. 1A is a schematic of a prior art butterfly valve with flat leaflets in the mitral position shown in both the open and closed positions.

Referring now to FIG. 1A and 1B, a prior art flat butterfly bileaflet valve is shown in FIG. 1A having flat leaflets 50 and 52 which are positioned in the mitral annulus between the left ventricle and the left atrium while the valve of the present invention using curved leaflets 14 and 16 is shown in FIG. 1B. The open position of the leaflets 50, 52 and 14 and 16 are shown in heavy dotted lines. The initial (closed) position is indicated by the light solid lines. Points M and M' are the extreme anterior and posterior points of the mitral annulus. Points P and P' are the pivot points. As previously indicated, the prior art valve of FIG. 1A in tests showed that the blood flow in the central channel between the leaflets 50 and 52 tends to be stagnant relative to the flow in the outside channels which may lead to valve thrombosis. On the other hand, the present design of FIG. 1B provides a venturi channel between the leaflets 14 and 16 which not only helps to open the leaflets 14 and 16 but to funnel additional flow into the channel between the leaflets 14 and 16.

Referring now to FIGS. 2A, 2B and 2C, the geometrical construction of a model valve of the present invention is shown in which the valve is shown in its closed configuration in FIG. 2A and in its open configuration in FIG. 2B and FIG. 2C. The valve is treated as symmetrical despite the asymmetry that is inherent in the mitral position. The valve is constructed starting from the points M and M' that define the mitral ring and the diameter of that ring is $d_m$.

The gap distance g separates the ends of the leaflets or occluders 14 and 16 from the mitral ring and from each other. Because all boundaries have an effective thickness (of about 2 mesh widths of the computational mesh used in the computer model), these gaps are effectively closed when the valve is in the closed position. The chords AB and A'B' of the leaflets 14 and 16 are constructed in the closed position at an angle $\theta_0$ to the line MM' that defines the level of the mitral ring. Throughout, we take $\theta_0 = 25°$. This 25 degrees initial angle of the leaflets 14 and 16 relative to the mitral ring was chosen to approximately minimize the volume swept out by the leaflets during their opening or closure movement. This result is independent of the position of the pivot points P and P' and the curvature of the leaflets 14 and 16 and roughly minimizes the volume swept for leaflets having a maximum opening angle in the range between 85 degrees and 90 degrees, which opening angle will be further discussed herein.

The occluders 14 and 16 themselves are the circular arcs APB and A'P'B' with centers of curvature at 0 and 0', respectively, on the upstream (atrial) side of the valve. Let $r_o$ = radius of curvature of the occluders
$d_o$ = length of AB = chord of the occluders $R = r_o/d_o$
$C = 1/R$ Then R is the dimensionless radius of curvature, and C, the reciprocal of R, is the dimensionless curvature. The special case of a flat valve is characterized by $r_o = \infty$, $R = \infty$ and $C = 0$. In the flat case the occluder coincides with the chord AB. We shall use the parameter C to characterize the curvature of the valve. This is one of the principal design parameters.

Another important parameter is the position of the pivot points such as P (which remains fixed relative to the points M and M' as the occluder rotates). Its location is defined by measuring arc length from the outer border of the occluder. Let $s_p$ = length of the arc AP
$s_o$ = length of arc APB
$S_P = s_p/s_o$ Then $S_P$ gives the position of the pivot point in dimensionless form. By definition, $0 < S_P < 1$, with the larger values of $S_P$ corresponding to pivot points which are closer to the center of the valve apparatus. In practice, $S_P$ must be chosen, as will be discussed hereafter, in the neighborhood of ⅔ to achieve reasonable performance. If $S_P < 0.5$, the valve does not open at all.

The final design parameter is the maximum angle of opening of the valve. This angle, $\theta_{max}$, is the angle of the chords AB and A'B' to the plane of the mitral ring, as shown in FIG. 2B. Most of the computations in the current study were conducted with $\theta_{max} = 85°$ or $90°$, as will be more fully discussed hereinafter.

Two other of the performance criteria are the net stroke volume (SV) and the mean forward pressure difference ($\overline{\Delta p}$). The net stroke volume is defined as the net volume of blood crossing the plane of the mitral annulus during the time interval when the valve is open. It is the difference between the forward volume and the regurgitant volume associated with the closure movement of the occluders 14 and 16.

The mean forward pressure difference is defined by the formula $$\overline{\Delta p} = \frac{1}{T} \int_0^T (p_{LA}(t) - p_{LV}(t)) dt$$

where $p_{LA}(t)$ and $p_{LV}(t)$ are the left atrial and left ventricular pressures at time t. The time $t = 0$ is defined as the onset of mitral flow, and $t = T$ is defined as the time of the first zero-crossing of the mitral flow, which occurs during early ventricular systole. The rationale for this choice of times is that it eliminates an inertial component of the pressure difference. These two performance criteria are combined into a single benefit/cost ratio: $SV/\overline{\Delta p}$. This seems appropriate because SV and $\overline{\Delta p}$ are not really independent measures of performance.

The following performance criterion is concerned with valve thrombosis. Let $Q_{ant}(t)$ be the volume rate of flow crossing the line MP in FIG. 2C, let $Q_{cent}(t)$ be the volume rate of flow crossing the line PP' and let $Q_{post}(t)$ be the volume rate of flow crossing P'M'. Thus $Q_{ant}$, $Q_{cent}$, $Q_{post}$ are the anterior 60, central 62 and posterior 64 flows, respectively. Let $A_{ant}$, $A_{cent}$, and $A_{post}$ be the cross-sectional areas of the three openings of the valve. That is, let $A_{ant}$ = (length of MP)·$L_0$
$A_{cent}$ = (length of PP')·$L_0$
$A_{post}$ = (length of P'M')·$L_0$ where $L_0 = 1.84$ cm is a reference length ($L_0$ is the diameter of the mitral ring) that is used to convert length in the two-dimensional model to cross-sectional area.

Next define $v_{ant}(t) = Q_{ant}(t)/A_{ant}$
$v_{cent}(t) = Q_{cent}(t)/A_{cent}$
$v_{post}(t) = Q_{post}(t)/A_{post}$ The quantities $v_{ant}(t)$, $v_{cent}(t)$, $v_{post}(t)$ have units of velocity; they are the spatially averaged velocity at time t in each of the three openings of the valve. (These velocities are independent of $L_0$ because both Q and A contain factors of $L_0$ in their definition.)

The maximum over time of the velocities $v_{ant}$, $v_{cent}$, and $v_{post}$ will be designated by the symbol *. Thus $$V_{ant}^* = \text{Max}_t\{v_{ant}(t)\}$$

$$V_{cent}^* = \text{Max}_t\{v_{cent}(t)\}$$

$$V_{post}^* = \text{Max}_t\{v_{post}(t)\}$$

These peak velocities are important because a low peak velocity implies stagnation and hence a tendency to thrombosis. To avoid thrombosis altogether, we adopt a worst-case criterion. Let $$v_{min}^* = \text{Min}\{v_{ant}^*, v_{cent}^*, v_{post}^*\}$$

If $v^*_{min} = 30$ cm/sec, for example, then a velocity of at least 30 cm/sec is achieved at some time during filling in each opening of the valve. We seek design parameters that make $v^*_{min}$ as large as possible.

Figure 3:
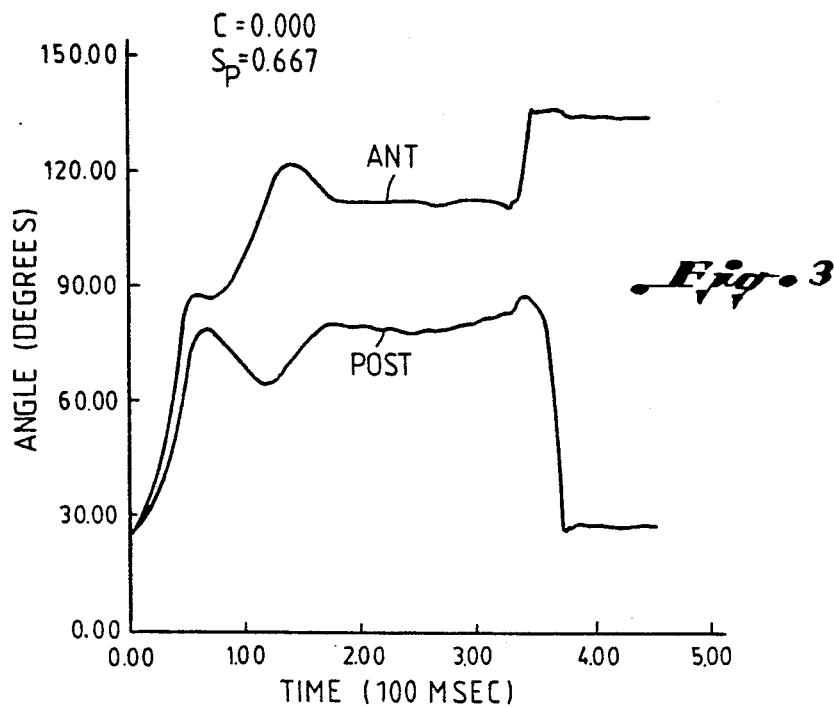
FIG. 3 is a graph illustrating the opening angles of the anterior and posterior leaflets of a conventional bileaflet butterfly flat valve as a function of time.

In the case of single-disc valves, good performance can be achieved without any built-in constraint on the opening angle. For the curved butterfly bileaflet mitral valve, however, we were unable to find any combination of pivot point and curvature for which the valve would exhibit good performance without a constraint. The difficulty is related to asymmetrical movement of the leaflets 14 and 16 which, in turn, must be caused by the asymmetry of the mitral position, since the valve is symmetrical. FIG. 3 shows the opening angle as a function of time for a prior art flat, bileaflet valve effectively unconstrained ($\theta_{max} = 135°$) pivoted at $S_P = 0.67$. Note that the anterior leaflet opens much faster than the posterior leaflet and that it becomes caught in the open position. This makes the valve incompetent. Competent performance can be achieved by reducing $S_P$, but then the posterior leaflet fails to open sufficiently and the valve is very stenotic. One way out of this dilemma would be to construct an asymmetrical valve in which the asymmetry of the valve compensates for the asymmetry of the mitral position. In the present study, which is restricted to symmetrical valves, the only solution is to impose a constraint on the maximum opening angle. With such a constraint, and with the pivot point and curvature in an appropriate range both leaflets 14 and 16 hit the constraint (albeit at slightly different times) and the open configuration of the valve is symmetrical.

Figure 4A:
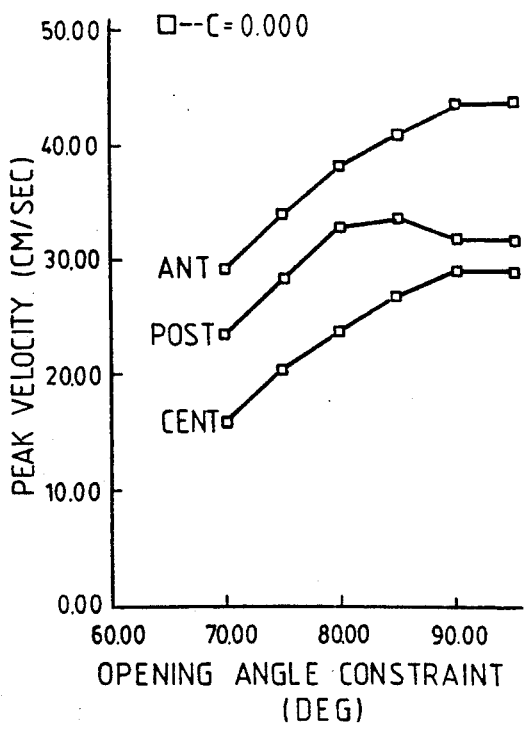
FIG. 4A is a graph illustrating the peak velocity in each of the three openings of a valve as a function of opening angle constraint on a conventional valve with flat leaflets.
Figure 4B:
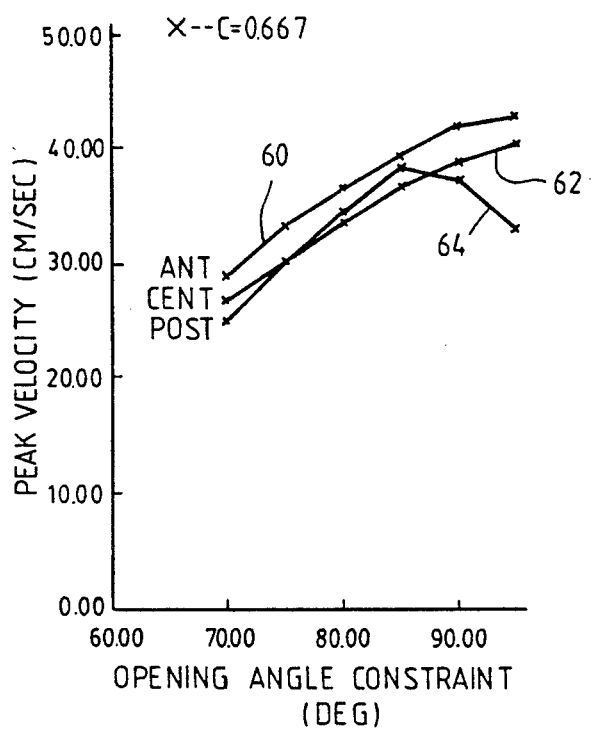
FIG. 4B is a graph similar to that of 4A but with the valve of the present invention with curved leaflets.

Valve performance has not been systematically optimized with respect to maximum opening angle $\theta_{max}$. Instead we have chosen two reasonable values of $\theta_{max}$ and conducted the rest of the study with these values fixed. The motivation for this choice is shown in FIG. 4, in which peak velocity is plotted in each of the three openings 60, 62, 64 of the valve as a function of the opening angle constraint. The results are shown both for the flat valve of FIG. 1A (FIG. 4A) and for a curved valve of the present invention of FIG. 1B (FIG. 4B). The pivot point in both cases is $S_P=0.67$.

The goal is to make the minimum of the three peak velocities as large as possible. For the flat valve (FIG. 4A) at this pivot point, the minimum peak velocity always occurs in the central opening of the valve. (This has also been observed in vitro.) This minimum peak velocity builds up to its largest value at about a 90 degree opening angle constraint and then levels off. (Competent performance cannot be maintained much beyond 90 degrees, since the anterior leaflet tends to get stuck in the open position and fail to close.) For the curved valve of the present invention, FIG. 4B, the situation is somewhat more complicated, since the smallest peak velocity occurs first in the posterior opening 64, then in the central opening 62, and finally again in the posterior opening 64 as the maximum opening angle increases from 70 degrees to 90 degrees. Here the minimum of the three peak velocities is largest where the center and posterior velocities cross near a maximum opening angle of 85 degrees. These results suggest that opening angle constraints in the range 85 degrees to 90 degrees are most likely to produce good performance.

For the rest of this study, we fix the maximum opening angle at $\theta_{max}=85°$ or $\theta_{max}=90°$. The figures which follow will show results for these two values of $\theta_{max}$ side by side.

Figure 5:
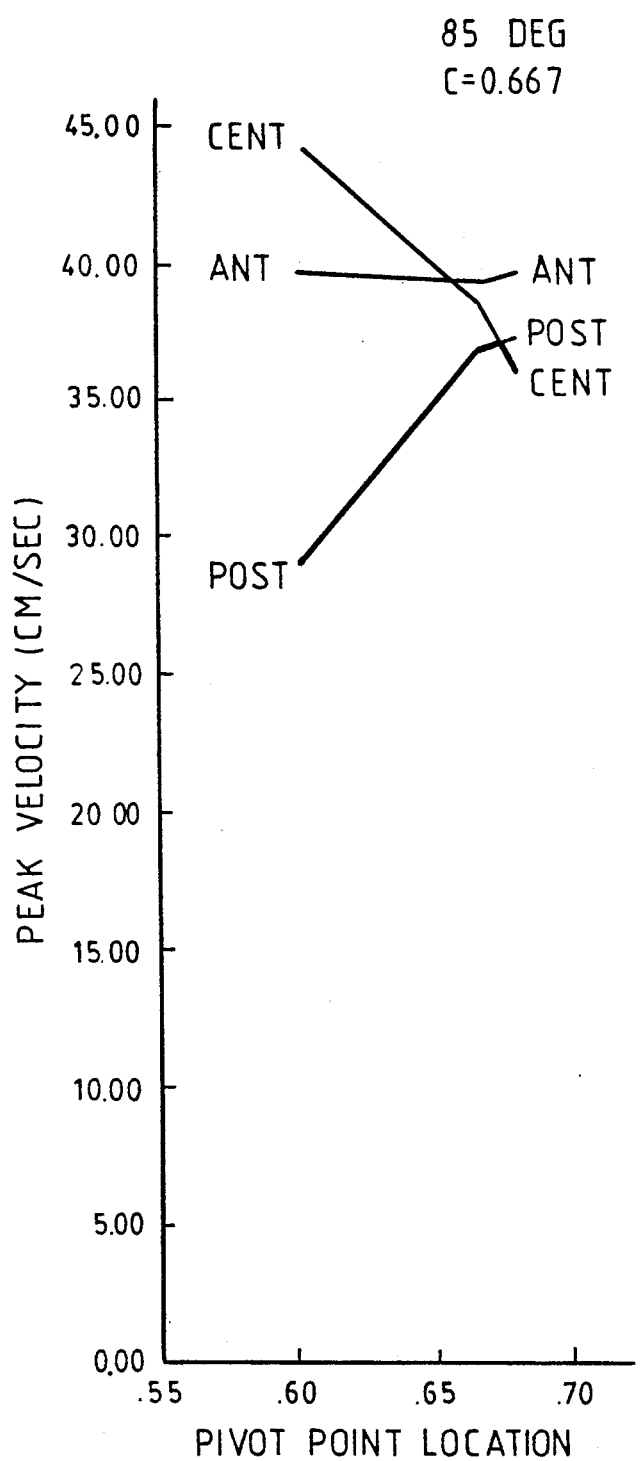
FIG. 5 is a graph illustrating the peak velocity in each of the three openings of the valve of the present invention as a function of the axis pivot point location.

Minimum peak velocity ($v^*_{min}$) varies as a function of pivot point ($S_P$) and (C). FIG. 5 shows a typical plot of peak velocity in the three openings, 60, 62, and 64, of the valve as a function of pivot point with curvature held fixed (in this case $C=0.667$). Note that the different peak-velocity curves intersect and that the minimum peak velocity (heavy line) is largest at the pivot point where the posterior and central peak velocities are equal. In subsequent figures, we plot only the minimum peak velocity without specifying the opening of the valve in which it occurs.

Figure 6A:
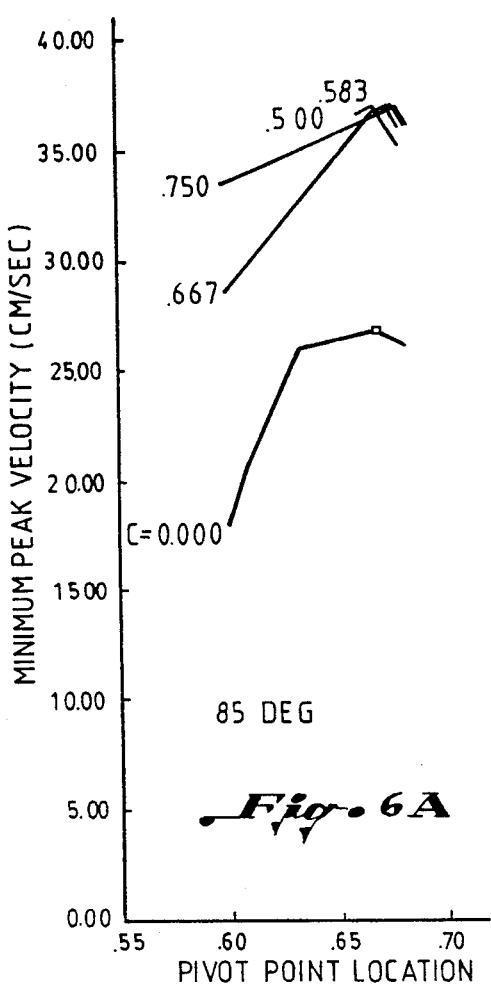
FIG. 6A is a graph of the minimum peak velocity as a function of the pivot point location for various leaflet curvatures with a maximum valve opening of 85 degrees.
Figure 6B:
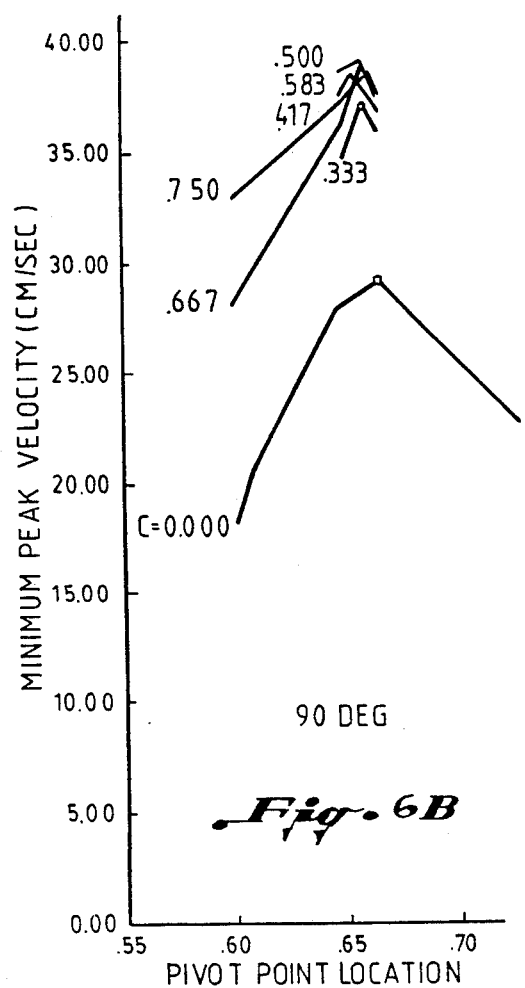
FIG. 6B is a graph similar to FIG. 6A for a valve opening of 90 degrees.

FIGS. 6A and 6B plot the minimum peak velocity ($v^*_{min}$) as a function of pivot point ($S_P$) at various curvatures (C=0, 0.333, 0.417, 0.500, 0.583, 0.667, 0.750). There are two remarkable points. First, at every curvature there is a pivot point that maximizes the minimum peak velocity. These pivot points are clustered around $S_P=0.67$. Second, the curved valves have substantially higher values of $v^*_{min}$ (minimum peak velocity) than the flat valves of FIG. 1A. In fact, by curving the occluders 14 and 16, as shown in FIG. 1B, one can increase $v^*_{min}$ by about 10 cm/sec (more than 30%) in comparison with the best flat valve.

Figure 7A:
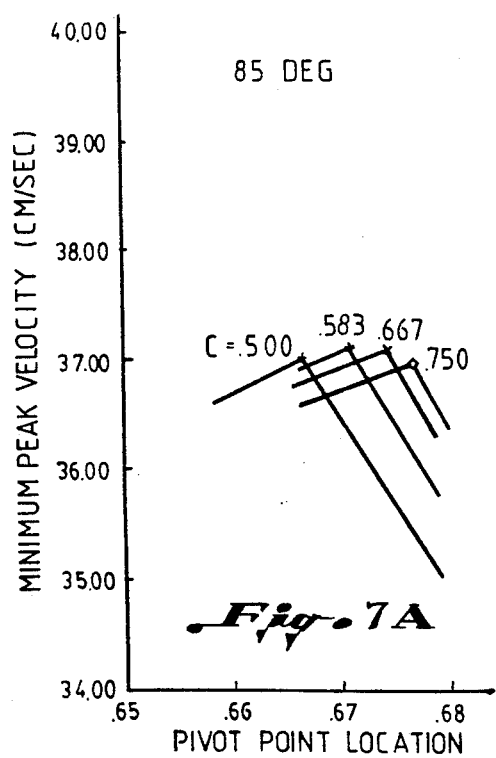
FIGS. 7A and 7B are enlarged views of FIG. 6A and 6B, respectively.
Figure 7B:
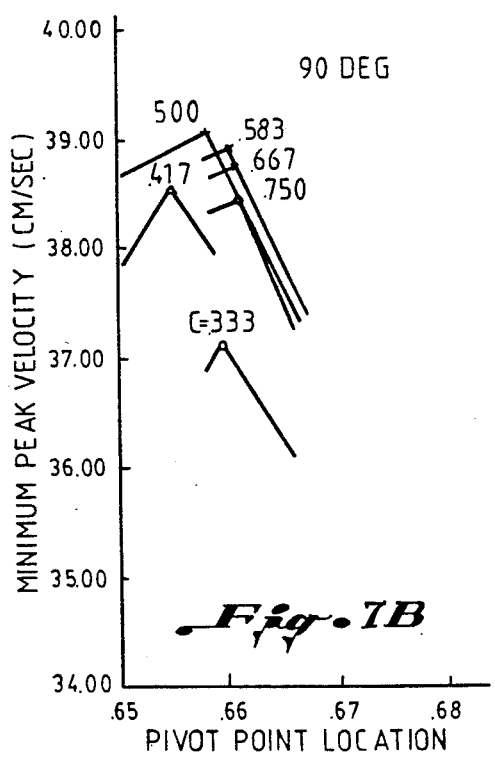
Figure 8A:
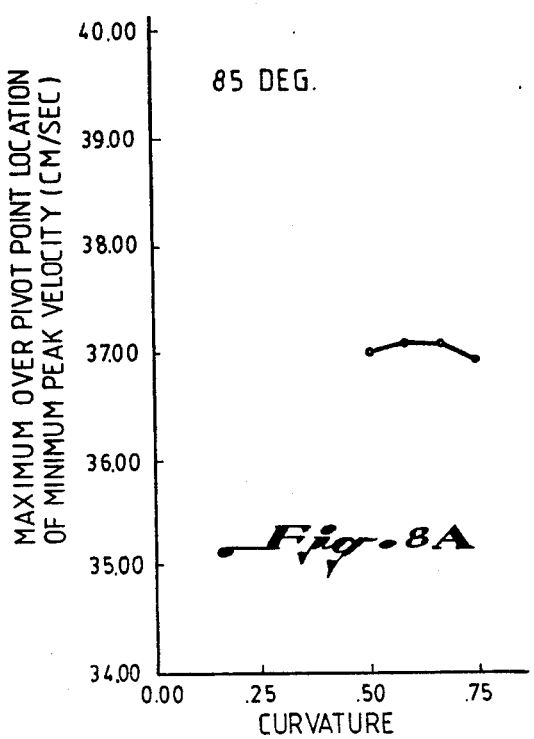
FIG. 8A is a graph of maximum over pivot point location of minimum peak velocity as a function of leaflet curvature with a maximum valve opening of 85 degrees.
Figure 8B:
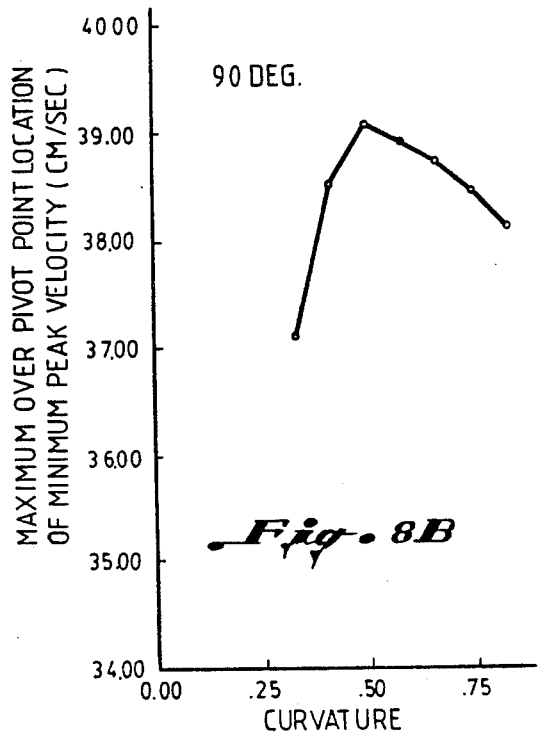
FIG. 8B is a graph similar to FIG. 8A but with a valve maximum opening of 90 degrees.

The optimal combination of pivot point and curvature can be found by expanding FIGS. 6A and 6B in the neighborhood of the best valves. The result is shown in FIGS. 7A and 7B. For each curvature there is an optimal pivot point, denoted by $S^{**}_P(C)$ which maximizes $v^*_{min}$. The value of $v^*_{min}$ at This optimal pivot point is denoted by $v^{}_{min}(C)$. FIGS. 8A and 8B are plots of $v^{}_{min}$ as a function of C.

The values of $v^{}_{min}$ and $S^{}_P$ are listed in Table I (FIGS. 12A). For each value of $\theta_{max}$ there is one curvature, denoted by $C_{opt}$, which results in the largest value of $v^{}_{min}$. The values of $C_{opt}$, $S^{}_P(C_{opt})$, and $v^{**}_{min}$ ($C_{opt}$) for $\theta_{max}=85°$ and 90° are listed in Table II (FIG. 12B). These values define the two best valves in the study.

Figure 9A:
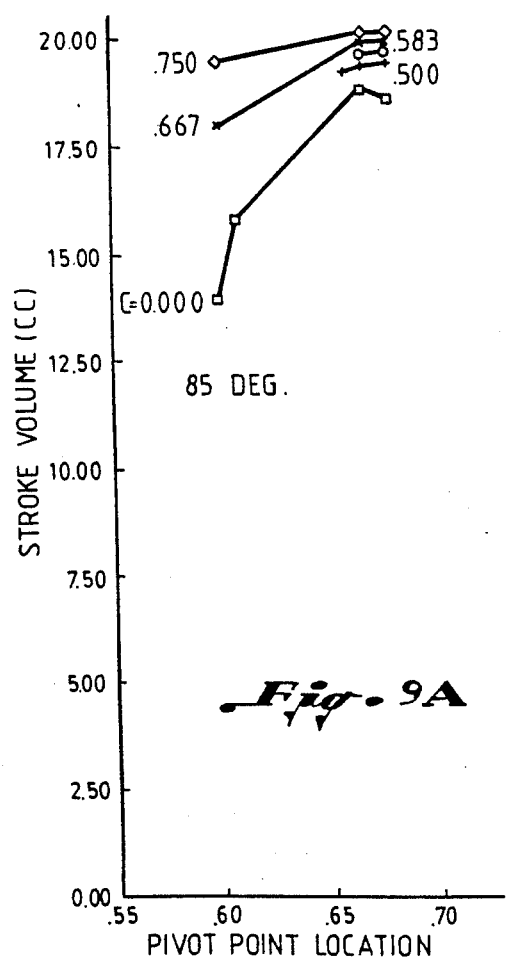
FIG. 9A is a graph of stroke volume as a function of pivot point location for various leaflet curvatures with a maximum valve opening of 85 degrees.
Figure 9B:
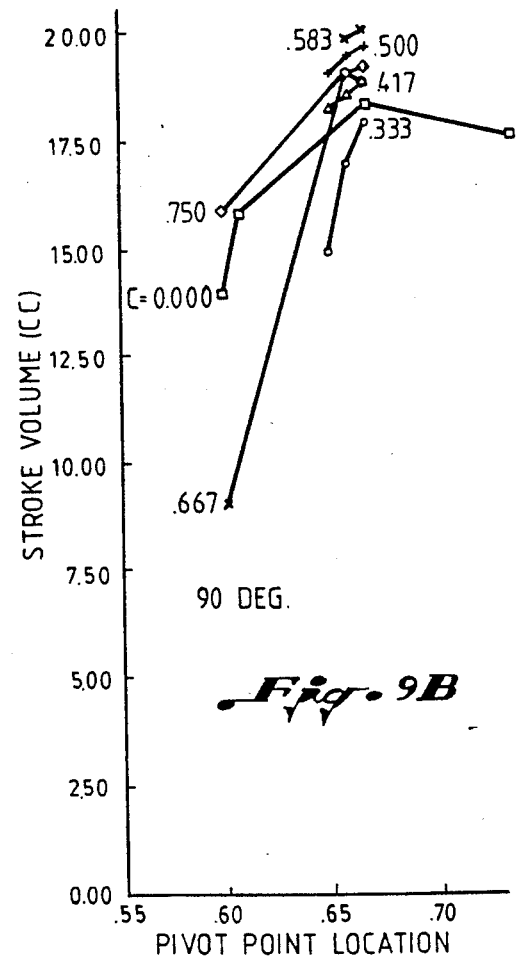
FIG. 9B is a graph similar to that of FIG. 9A for a maximum valve opening of 90 degrees.
Figure 10A:
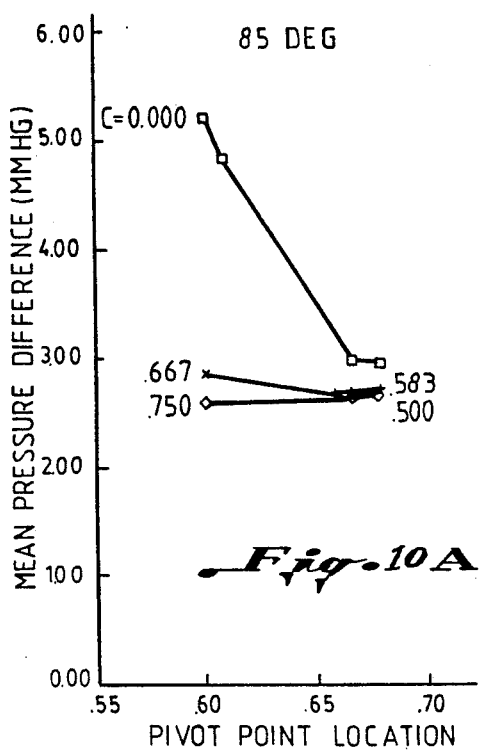
FIG. 10A is a graph of mean transvalvular pressure difference as a function of pivot point location for various leaflet curvatures with a maximum valve opening of 85 degrees.
Figure 10B:
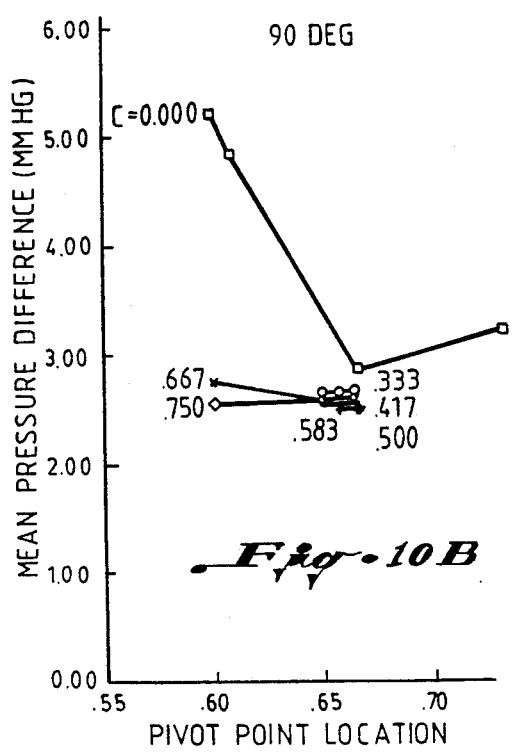
FIG. 10B is a graph similar to that of FIG. 10A but with a maximum valve opening of 90 degrees.
Figure 11A:
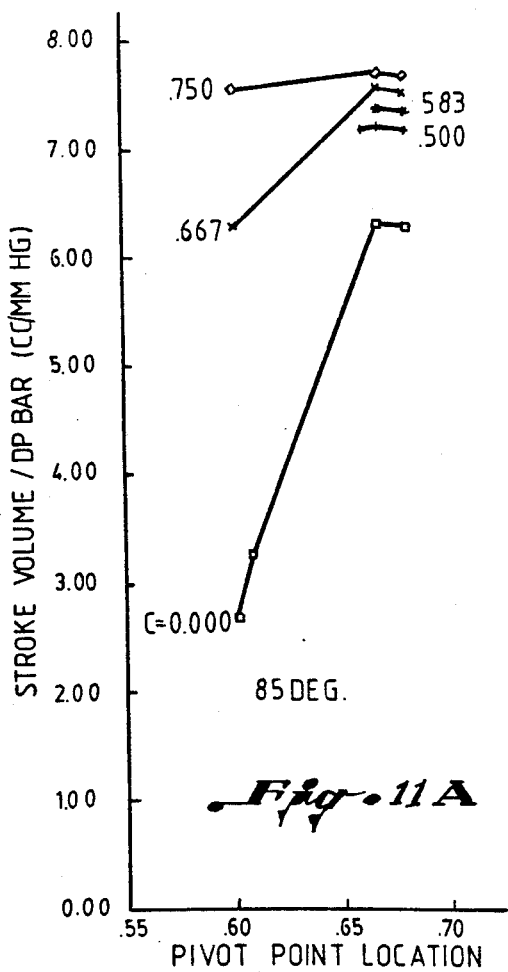
FIG. 11A is a graph of the net stroke volume/mean forward pressure difference or hemodynamic benefit/cost ratio as a function of pivot point location for various leaflet curvatures with a maximum valve opening of 85 degrees.
Figure 11B:
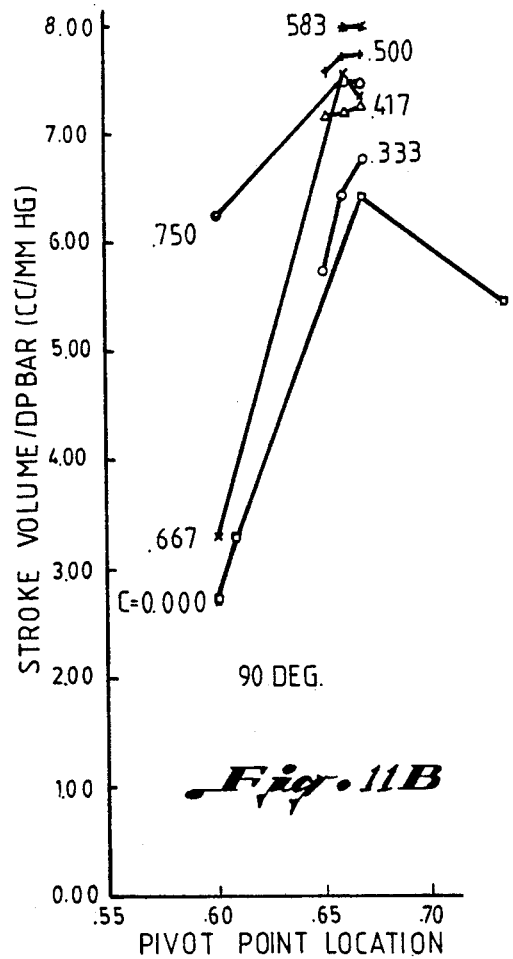
FIG. 11B is a graph similar to that of FIG. 11A but with a maximum valve opening of 90 degrees.

Hemodynamic performance is another important criteria. The foregoing choice of an optimal valve was based on considerations relating to stagnation and thrombosis. Considering the design problem from a hemodynamic pressure-flow) viewpoint, FIGS. 9A and 9B plot the stroke volume (i.e., the net volume of blood crossing the mitral valve during one heartbeat) as a function of pivot point at several curvatures FIGS. 10A and 10B plot the mean pressure difference across the valve in the same way. FIGS. 11A and 11B combine these two performance criteria into a single benefit/cost ratio: the quotient of the net stroke volume and the mean pressure difference across the valve.

At each curvature in FIGS. 11A and 11B there is an optimal pivot point. As before these optimal pivot points are clustered in the neighborhood of $S_P=0.667$. Starting from the flat valve, C=0.000, and increasing the curvature, we find that performance (the quotient of stroke volume and mean pressure difference) first improves dramatically and then falls off. Of the valves that we have tested, those with the best hemodynamic performance are listed in Table III (FIG. 12C).

In choosing the best overall valve, how much weight should be given to the minimum peak velocity (a criterion related to thrombosis) in comparison with the hemodynamic benefit/cost ratio of the net stroke volume divided by the mean pressure difference? Fortunately, there is no real need to answer this question because the two criteria lead to very similar conclusions (compare Table II and Table III). Moreover, we can adopt either criterion without much reduction in performance as measured by the other criterion. Suppose, for example, that we select the best valve by the criterion of maximizing $v^*_{min}$ (the minimum peak velocity). While this valve is suboptimal with respect to hemodynamic performance, the reduction in $SV/\overline{\Delta}p$ (the ratio of stroke volume to mean pressure difference) is only 3.8% for the valve with $\theta_{max}=85°$ and only 3.5% for the valve with $\theta_{max}=90°$. We are therefore in the fortunate situation of being able to select the valve which will minimize thrombosis while sacrificing very little in terms of hemodynamic performance.

In conclusion, a built-in constraint on the maximum angle of opening ($\theta_{max}$) is a necessary design feature of symmetrical butterfly bileaflet valves for the mitral position. The parameter $\theta_{max}$ should be set in the approximate range of 85 degrees 90 degrees.

With $\theta_{max}=85°$, the valve with least stagnation (technically, the valve with the largest value of $v^*_{min}$, the minimum peak velocity) has pivot point $S_P=0.671$ and curvature $C=0.583$. With $\theta_{max}=90°$, the valve with least stagnation has $S_P=0.658$ and $C=0.500$.

These valves are also nearly optimal from a hemodynamic viewpoint. That is, they come close (within 4%) to achieving the optimal value of net stroke volume divided by mean forward pressure difference.

The most important conclusion is that modest curvature of the leaflets 14 and 16 can make a substantial improvement in the performance of butterfly bileaflet valves. The type of curvature used is in a plane perpendicular to the pivot axes P and P' of the valve 10 and in a direction such that the open valve has a slight waist, like reversed parentheses: )(. When the optimal curvature is selected, the best valve of this type is superior to the best flat valve both with regard to the minimum peak velocity (which should be larger to prevent stagnation and thrombosis) and also with regard to the ratio of net stroke volume to mean forward pressure difference. For the two constraint angles that are considered (85° and 90°) the improvements in minimum peak velocity are 38% and 34%, while the improvements in the hemodynamic benefit/cost ratio are 16% and 20%. These conclusions are predictions made with the help of a computer model to produce the charts and tables of FIGS. 3–12.

The present invention, therefore, is well adapted to carry out the objects and attain the ends and advantages mentioned as well as others inherent therein. While presently preferred embodiments of the invention have been given for the purpose of disclosure, numerous changes in the details of construction and arrangement of parts may be made without departing from the spirit of the invention and the scope of the appended claims.

What is claimed is:

1. A heart valve prosthesis comprising, an annular valve body having a central passageway for the flow of blood therethrough from upstream to downstream, first and second curved symmetrical leaflets pivotally supported for movement between closed and open positions in the central passageway of the body, said leaflets when closed preventing flow through said passageway and when open defining a posterior opening, a central opening, and an anterior opening through the passageway, each curved leaflet having a concave and a convex side, eccentric position axis means pivotally supporting said curved leaflets, said leaflets being curved in a plane normal to the eccentric axis and positioned with the convex sides of the leaflets facing each other when the leaflets are in the open position, and said concave sides of the leaflets facing upstream when in the closed position, means in the body for limiting the maximum angle of opening of the leaflets to approximately 90° from a transverse plane to the central passageway, and said first and second leaflets are pivotally supported at a position and have a curvature for maximizing the minimum peak velocity flowing through said openings and for maximizing the ratio of the net stroke volume to the mean pressure difference across the valve during forward flow thereby avoiding stagnation in all of said openings of the valve and reducing the pressure drop that is required to move fluid through the valve.

2. The apparatus of claim 1 wherein the leaflets are circularly curved.

3. The apparatus of claim 1 wherein the first and second leaflets are pivotally supported along an axis located approximately two-thirds of the greatest distance from an arcuate body-contacting edge to a leaflet-mating edge of each leaflet.

4. The apparatus of claim 3 wherein the curvature C of the leaflets is in the range of approximately 0.4 to 0.7 wherein $C = d_o/r_o$, and $r_o =$ the radius of curvature of the leaflets, and $d_o =$ the length of the chord of the leaflets.

5. The apparatus of claim 1 wherein the curvature C of the leaflets is in the range of approximately 0.4 to 0.7 wherein $C = d_o/r_o$, and $r_o =$ the radius of curvature of the leaflets, and $d_o =$ the length of the chord of the leaflets.

* * * * *